US008133885B2

United States Patent
Plate et al.

(10) Patent No.: US 8,133,885 B2
(45) Date of Patent: Mar. 13, 2012

(54) NON STEROIDAL GLUCOCORTICOID RECEPTOR MODULATORS

(75) Inventors: Ralf Plate, Oss (NL); Guido Jenny Rudolf Zaman, Oss (NL); Pedro Harold Han Hermkens, Oss (NL); Christiaan Gerardus Johannes Maria Jans, Oss (NL); Rogier Christian Buijsman, Oss (NL); Adrianus Petrus Antonius De Man, Oss (NL); Paolo Giovanni Martino Conti, Oss (NL); Scott James Lusher, Oss (NL); Willem Hendrik Abraham Dokter, Oss (NL)

(73) Assignee: Merck Sharp & Dohme Corp., Rahway, NJ (US)

( * ) Notice: Subject to any disclaimer, the term of this patent is extended or adjusted under 35 U.S.C. 154(b) by 784 days.

(21) Appl. No.: 11/816,113

(22) PCT Filed: Feb. 14, 2006

(86) PCT No.: PCT/EP2006/050906
§ 371 (c)(1),
(2), (4) Date: Oct. 21, 2008

(87) PCT Pub. No.: WO2006/084917
PCT Pub. Date: Aug. 17, 2006

(65) Prior Publication Data
US 2009/0062262 A1    Mar. 5, 2009

(30) Foreign Application Priority Data

Feb. 14, 2005 (EP) .................... 05101086

(51) Int. Cl.
*A61P 29/00* (2006.01)
*A61K 31/551* (2006.01)
*C07D 471/04* (2006.01)
(52) U.S. Cl. ....................... 514/219; 540/555
(58) Field of Classification Search .......... 514/219; 540/555
See application file for complete search history.

(56) References Cited

U.S. PATENT DOCUMENTS
4,054,572 A    10/1977   Van Der Burg

FOREIGN PATENT DOCUMENTS
WO    WO 03/084963    10/2003
WO    WO 03/104195    12/2003

OTHER PUBLICATIONS

International Search Report and Written Opinion, dated Apr. 20, 2006, which issued during the prosecution of International Application No. PCT/EP2006/050906.
Baxter, J.D., "Advances in Glucocorticoid Therapy," *Advances in Internal Medicine 45* (2000) 317-349.
Hyde et al., "Lipopolysaccharide-Tumor Necrosis Factor-Glucocorticoid Interactions during Cecal Ligation and Puncture-Induced Sepsis in Mature versus Senescent Mice," *Infection and Immunity 60* (1992) 976-982.
Karin, M. "New Twists in Gene Regulation by Glucocorticoid Receptor: Is DNA Binding Dispensable?" *Cell 93* (1998) 487-490.
Rewcastle et.al., "Potential Antitumor Agents. 51. Synthesis and Antitumor Activity of Substituted Phenazine-1-carboxamides," *J. Med. Chem 30* (1987) 843-851.
Trentham, et.al., "Autoimmunity to Type II Collagen: An Experimental Model of Arthritis," *J Exp Med 146* (1977) 857-868.

*Primary Examiner* — Brenda Coleman
(74) *Attorney, Agent, or Firm* — Yong Zhao; Valerie J. Camara

(57) ABSTRACT

The present invention relates to compounds having general Formula (I) or a pharmaceutically acceptable salt thereof. The present invention also relates to pharmaceutical compositions comprising said compounds and the use of these derivatives to modulate glucocorticoid receptor activity.

11 Claims, No Drawings

NON STEROIDAL GLUCOCORTICOID RECEPTOR MODULATORS

CROSS REFERENCE TO RELATED APPLICATION

This application claims priority based on International Patent Application No. PCT/EP2006/050906, filed on Feb. 14, 2006.

FIELD OF THE INVENTION

The present invention relates to glucocorticoid receptor modulating compounds as well as to the use of these compounds in therapy.

BACKGROUND OF THE INVENTION

Intracellular receptors are a class of structurally related proteins involved in the regulation of gene proteins. Steroid receptors are a subset of these receptors, including the glucocorticoid receptor (GR), progesterone receptor (PR), androgen receptor (AR), estrogen receptor (ER), and mineralocorticoid receptor (MR). Regulation of a gene by such receptors or factors requires the intracellular receptor and a corresponding ligand which has the ability to selectively bind to the receptor in a way that affects gene transcription.

The current steroidal glucocorticoid receptor modulators (glucocorticoids) like prednisolone a.o. are very effective anti-inflammatory agents that are currently used in over 100 indications in the fields of Rheumatology, Hematology, Pulmology, Dermatology, Gastro-enterology, Endocrinology, Neurology, and Nephrology. Indications treated include Rheumatoid Arthritis (RA), Inflammatory Bowel Disease (IBD), Lupus, allergies, asthma, psoriasis and many others (J. D. Baxter, Advances in Internal Medicine 45; 317-349; 2000). Anti-inflammatory effects of these compounds are thought to be mediated through an inhibition of the expression of pro-inflammatory mediators like adhesion molecules, cytokines, chemokines and enzymes by a mechanism that involves the interaction of the ligand-bound GR with transcription factors. This mechanism is referred to as transrepression (M. Karin, Cell 93; 487-490; 1998).

The use of current steroidal glucocorticoids is accompanied by metabolic and other side effects (e.g. diabetes, hypertension, osteoporosis, muscle wasting, a.o.). Part of these side effects are thought to be mediated through the direct interaction of the ligand bound GR to glucocorticoid responsive elements (GRE's) on the DNA of target genes and the subsequent induction of gene expression (J. D. Baxter, Advances in Internal Medicine 45; 317-349; 2000; M. Karin, Cell 93; 487-490; 1998). Another part of these side effects might be due to cross-reactivity with other steroidal receptors, like the mineralcorticoid (MR) or the progesterone receptor (PR).

Non-steroidal glucocorticoids have no molecular structural similarity with steroids and therefore one might also expect differences in physicochemical properties, pharmacokinetics (PK) parameters, tissue distribution (e.g. CNS versus peripheral) and more importantly non-steroidal glucocorticoids may show no/less cross-reactivity to other steroid receptors or may show no/less metabolic or other side effects.

SUMMARY OF THE INVENTION

The present invention provides non-steroidal compounds that modulate glucocorticoid receptor activity. More particularly, the present invention provides high affinity non-steroidal compounds for GR binding which show anti-inflammatory effects in vitro and in vivo. According to the present invention compounds are provided having a general formula I, or a prodrug thereof, or a pharmaceutically acceptable salt thereof.

DETAILED DESCRIPTION OF THE INVENTION

The present invention provides non-steroidal compounds that modulate glucocorticoid receptor activity. More particularly, the present invention provides high affinity non-steroidal compounds which are agonists, partial agonists or antagonists of the glucocorticoid receptor. According to the present invention compounds are provided having a general Formula I, Formula I or a pharmaceutically acceptable salt thereof.

In this Formula, the R groups have the following meanings:

$R_1$ is H or (1-4C)alkyl;
$R_2$ is —C(O)$R_{15}$ or —S(O)$_2R_{15}$
$R_3$ is H, (1-4C)alkyl or —O$R_{16}$
$R_4$ is H, (1-4C)alkyl or —O$R_{16}$
$R_6$ is H or —C(H)NO$R_{16}$;
$R_7$ is H or halogen, cyano;
(1-6C)alkyl, (2-6C)alkenyl or (2-6C)alkynyl, all three optionally substituted with OH, halogen or NH$_2$;
—C(H)NO$R_{16}$, —O$R_{16}$, —C(O)$R_{16}$, or —C(O)O$R_{16}$;
$R_8$ is H, cyano, halogen, nitro;
(1-6C) alkyl, (2-6C)alkenyl, (2-6C)alkynyl or —O(1-6C)alkyl, all optionally substituted with amino, hydroxyl or halogen;
(hetero)aryl, optionally substituted with cyano, halogen, (1-4C)alkyl, (1-4C)alkoxy, (1-4C)alkoxy(1-4C)alkyl;
—C(H)NO$R_{16}$, —C(O)NH$R_{17}$, —C(O)$R_{18}$, —C(O)O$R_{19}$, —NHC(O)$R_{20}$, —NHS(O)$_2R_{21}$; or —C(1-4C)alkyl-NO$R_{21}$;
$R_9$ is H, halogen, cyano or (1-4C)alkyl optionally substituted with halogen;
$R_{10}$ is H or (1-4C)alkyl;
$R_{11}$ is H;
$R_{12}$ is H, cyano or (1-4C)alkyl;
$R_{13}$ is H, (1-4C)alkyl, halogen or formyl;
$R_{14}$ is H, halogen, cyano, (1-4C)alkyl, (2-6C)alkenyl, C(O)$R_{21}$ or (hetero)aryl;
$R_{15}$ is H;
(1-6C)alkyl, (2-6C)alkenyl, (2-6C)alkynyl, —O(2-6C)alkyl, —O(2-6C)alkenyl or —O(2-6C)alkynyl, all optionally substituted with one or more OH, halogen, cyano or (hetero)aryl,
(hetero)aryl, optionally substituted with (1-4C)alkyl, halogen, cyano, nitro or amino NH$_2$, (di)(1-4C)alkylamino, (1-4C)alkyl(1-4C)alkoxyamine, (1-4C)alkylthio(1-4C) alkyl or (1-4C)alkoxy(1-4C)alkyl;

$R_{16}$ is H, (1-6C)alkyl, (2-6C)alkenyl or (2-6C)alkynyl;
$R_{17}$ is H,
(1-6C)alkyl, optionally substituted with halogen, (1-4C)alkoxy or (hetero)aryl, optionally substituted with halogen, (1-4C)alkyl or (1-4C)alkoxy;
(3-6C)cycloalkyl or
(hetero)aryl, optionally substituted with halogen, (1-4C)alkyl or (1-4C)alkoxy;
$R_{18}$ is H, $NH_2$, —C(O)$R_{21}$ or (1-4C)alkyl, optionally substituted with OH, halogen, cyano or —S(1-4C)alkyl;
$R_{19}$ is H or (1-6C)alkyl, optionally substituted with OH or halogen;
$R_{20}$ is H,
(1-6C)alkyl or (2-6C)alkenyl, both optionally substituted by halogen, O(1-6C)alkyl, (hetero)aryl, optionally substituted with (1-4C)alkyl or halogen;
(3-6C)cycloalkyl; (1-6C)alkoxy; (1-6C)alkenyloxy; or
(hetero)aryl, optionally substituted with (1-4C)alkyl), $NH_2$, —NH(1-6C)alkyl or —NH(hetero)aryl;
and
$R_{21}$ is H or (1-6C)alkyl;

Thus, it has now been found, that the foregoing class of compounds according to Formula I or pharmaceutically acceptable salts thereof, have glucocorticoid receptor modulatory activity.

The term (1-6C)alkyl as used in the definition of the invention means a branched or unbranched alkyl group having 1-6 carbon atoms, for example methyl, ethyl, propyl, isopropyl, butyl, sec-butyl and tert-butyl, pentyl and hexyl. Preferred are (1-4C)alkyl.

The term (1-4C)alkyl as used in the definition of the invention means a branched or unbranched alkyl group having 1-4 carbon atoms, for example methyl, ethyl, propyl, isopropyl, butyl, sec-butyl and tert-butyl. Preferred are methyl and ethyl. Most preferred is methyl.

The term (3-6C)cycloalkyl means a cyclic alkyl group having 3-6 carbon atoms.

The term halogen means fluorine, chlorine, bromine or iodine.

The term (2-6C)alkenyl means a branched or unbranched alkenyl group having 2-6 carbon atoms, such as ethenyl, 2-butenyl, pentenyl and hexenyl. Preferred are (2-4C)alkenyl.

The term (2-4C)alkenyl means a branched or unbranched alkenyl group having 2-4 carbon atoms, such as ethenyl and 2-butenyl.

The term (2-6C)alkynyl means a branched or unbranched alkynyl group having 2-6 carbon atoms, such as ethynyl, propynyl, butylyl, pentynyl and hexynyl. Preferred are (2-4C)alkynyl.

The term (2-4C)alkynyl means a branched or unbranched alkynyl group having 2-4 carbon atoms, such as ethynyl and propynyl.

The term —O(1-6C)alkyl means (1-6C)alkyloxy wherein (1-6C)alkyl has the previously defined meaning.

The term —O(2-6C)alkenyl means (2-6C)alkenyloxy wherein (2-6C)alkenyl has the previously defined meaning.

The term —O(2-6C)alkynyl means (2-6C)alkynyloxy wherein (2-6C)alkynyl has the previously defined meaning.

The term (1-4C)alkyloxy means an alkyloxy group having 1-4 carbon atoms, the alkyl moiety having the same meaning as previously defined. (1-2C)Alkyloxy groups are preferred.

The term (1-4C)alkoxy(1-4C)alkyl means a (1-4C)alkoxy attached to a (1-4C)alkyl group, both groups having the previously defined meanings.

The term (di)(1-4C)alkylamino means a amino moiety, with at least one, optionally two hydrogens replaced by a (1-4C) alkyl group as previously defined.

The term —S(1-4C)alkyl means a (1-4C)alkylthio group, the (1-4C)alkyl group having the previously identified meaning.

The term (1-4C)alkylthio(1-4C)alkyl means an (1-4C)alkylthio group attached to a (1-4C)alkyl group, both having the previously defined meanings.

The term aryl means 6 membered aromatic ring system.

The term heteroaryl means a 5 or 6 membered aromatic ring system containing at least one heteroatom selected from the group of N, O and S in a 5 membered ring and N in a 6 membered ring, such as pyridyl, pyrimidyl, tetrazolyl or thiadiazolyl.

The term (hetero)aryl means aryl or heteroaryl as defined above.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

The compounds of the present invention possess at least two chiral carbon atoms and may therefore be obtained as pure enantiomers, or as a mixture of enantiomers, or as a mixture of diastereomers. Methods for obtaining the pure enantiomers are known in the art, e.g crystallization of salts which are obtained from optically active acids and the racemic mixture, or chromatography using chiral columns. For separation of diastereomers, straight phase or reversed phase columns may be used.

The invention also relates to compounds according to Formula I wherein $R_7$ is H, halogen or —O$R_{16}$.

The invention also relates to compounds according to Formula I wherein $R_2$ is C(O)$R_{15}$.

In yet another aspect the invention relates to compounds according to Formula I wherein $R_7$ is H.

The invention further relates to those compounds wherein $R_{10}$ in Formula I is methyl.

The invention also relates to those compounds wherein $R_4$ in Formula I is H or (1-4C)alkyl.

Another aspect of the invention concerns compounds according to Formula I wherein $R_{16}$ is H or (1-6C)alkyl.

In another aspect the invention relates to compounds wherein $R_{14}$ is (1-4C)alkyl.

In yet another aspect the invention relates to compounds wherein $R_{15}$ is (1-4C)alkyl optionally substituted with halogen, cyano, nitro or amino.

In yet another aspect the invention relates to compounds wherein $R_{15}$ is (1-4C)alkyl optionally substituted with halogen.

In yet another aspect the invention relates to compounds of Formula I wherein $R_{15}$ is trifluoromethyl or (hetero)aryl, optionally substituted with (1-4C)alkyl.

The invention also relates to compounds of Formula I wherein $R_{15}$ is (hetero)aryl, optionally substituted with (1-4C)alkyl.

In a further aspect $R_{21}$ in the compounds according to Formula I is (1-4C)alkyl.

The invention also relates to compounds according to Formula I wherein $R_8$ is H, halogen, cyano, nitro, —C(O)$R_{18}$, —NHC(O)$R_{20}$ or (hetero)aryl, optionally substituted with cyano, (1-4C)alkyl, (1-4C)alkoxy, (1-4C)alkoxy(1-4C)alkyl or (hetero)aryl).

The invention also relates to compounds according to Formula I wherein $R_8$ is H, halogen, cyano, nitro, —C(O)$R_{18}$, —NHC(O)$R_{20}$ or (hetero)aryl, optionally substituted with cyano, (1-4C)alkyl, (1-4C)alkoxy or (1-4C)alkoxy(1-4C)alkyl.

The invention furthermore relates to those compounds wherein $R_8$ is H, cyano, pyridyl or nitro.

In another aspect the invention relates to compounds wherein $R_8$ is cyano, pyridyl or nitro. The invention also relates to compounds wherein $R_8$ is cyano.

In still another aspect the invention relates to compounds according to Formula I wherein $R_1$, $R_3$, $R_4$, $R_6$, $R_7$, $R_9$, $R_{11}$, $R_{12}$, $R_{13}$ and $R_{14}$ are H.

Yet another aspect of the invention concerns compounds wherein all specific definitions of the groups $R_1$ through $R_{21}$ as defined here above are combined in the compound of formula I.

The invention also resides in compounds according to Formula I which are highly specific for the glucocorticoid receptor. Specificity can be determined by testing the compound as described further on for the glucocorticoid receptor, with other well-known receptors such as progesterone receptor, androgen receptor, mineralocorticoid receptor or estrogen receptor.

Synthesis:

The sequence of steps to synthesize the compounds of the present invention are described in Scheme 1.

The compounds of the present invention can be prepared by first coupling 2-halonitroaryls of general structure 1, in which X has the meaning previously defined for halogens, with (N-alkyl)aniline derivatives.

The above mentioned reaction is typically conducted at elevated temperature in the presence of potassium carbonate and with, or without, the use of an organic solvent. 2-halonitroaryls of general structure 1 are either commercially available or easily accessible via synthetic routes, which are well documented in the literature. This reaction is reported in the literature by G. W. Rewcastle, et. al. J. Med. Chem., 30, 1987, 843. Alternatively, these reactions can be carried out in the presence of caesium carbonate, palladium acetate and BINAP to afford an analogous product.

Scheme 1

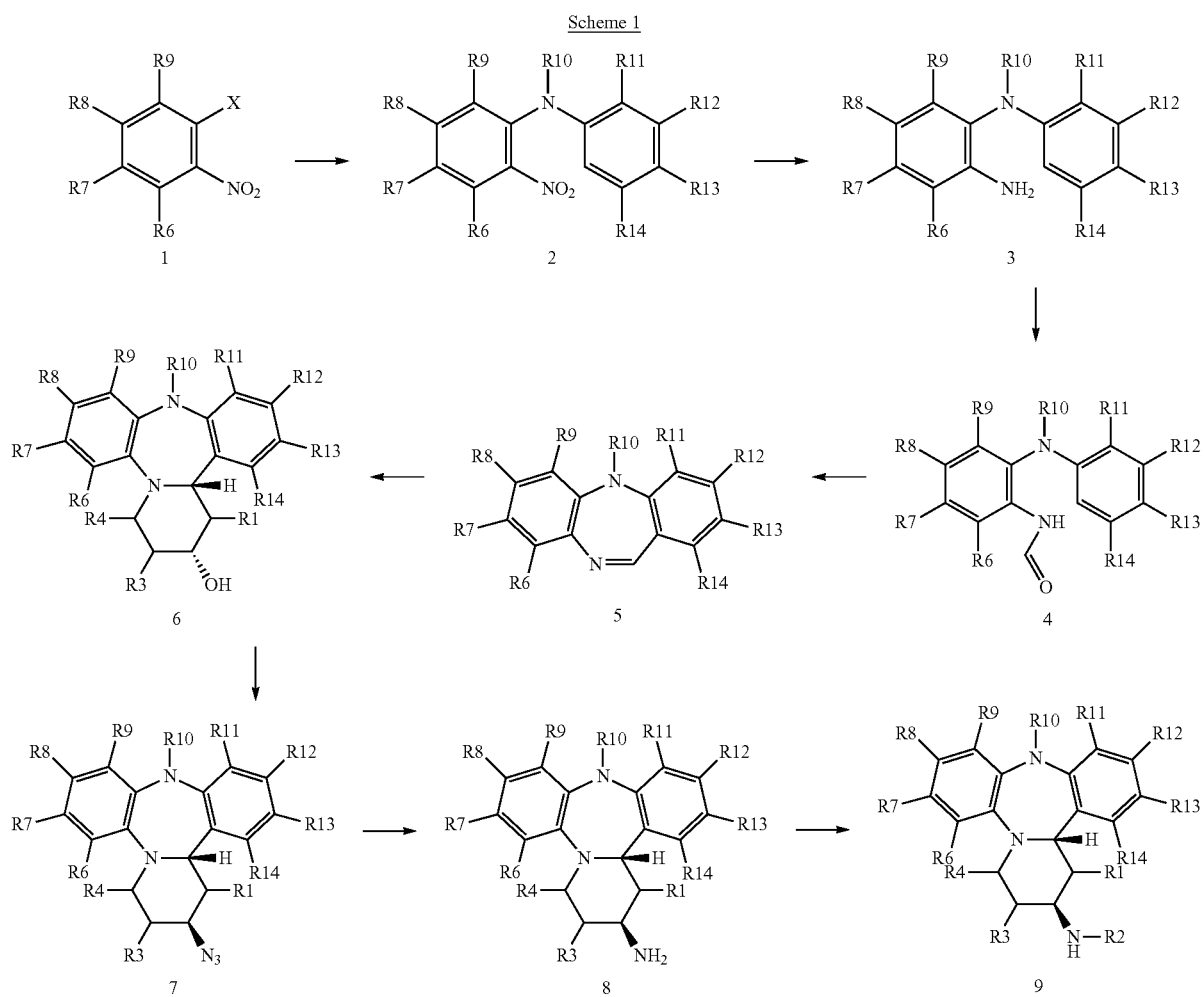

Compounds of general structure 2 can then be reduced to afford compounds of general structure 3.

The above mentioned reaction is typically conducted at ambient temperature in the presence of tin(II)chloride with an organic solvent then treated with hydroxide.

Compounds of general structure 3 can then be N-formylated to afford compounds of general structure 4.

The above mentioned reaction is typically conducted in refluxing formic acid, without the use of any organic solvent.

Compounds of general structure 4 can then be ring closed to form ring C and afford tricyclic compounds of general structure 5.

The above mentioned reaction is typically conducted at ambient temperature in the presence of phosphorous pentachloride, with the use of an organic solvent. Alternatively, these reactions can be carried out in the presence of polyphosphoric acid and phosphorous (V) trichloride oxide, without the use of any organic solvent, to afford the desired product.

Compounds of general structure 5 can then be reacted in a Hetero-Diels-Alder fashion to form the piperine ring and afford the tetracyclic compounds. These compounds can then be reduced in-situ to afford the tetracyclic alcohols of general structure 6, which are obtained mainly in the trans configuration.

The Diels-Alder reaction is typically conducted at reduced temperature in the presence of either trimethyl[(1-methylene-2-propenyl)oxy]silane, trimethyl[(1-methylene-2-butenyl)oxy]silane, or [(3-methoxy-1-methylene-2-propenyl)oxy]trimethylsilane (Danishefsky's diene) and ytterbium trifluoromethanesulfonate, with the use of an organic solvent. These crude products can then be reduced at ambient temperature in the presence of sodium borohydride, with the use of an organic solvent.

Compounds of general structure 6 can then reacted under Mitsunobu conditions to afford azide compounds of general structure 7.

The above mentioned reaction is typically conducted at ambient temperature in the presence of triphenylphosphine, diisopropylazodicarboxylate and diphenylphosphoryl azide, with the use of an organic solvent.

Compounds of general structure 7 can then be reduced to afford the free amine compounds of general structure 8. This reaction is typically conducted at ambient temperature in the presence of triphenylphosphine and water, with the use of an organic solvent. These compounds can then be coupled by general procedures with carboxylic acid derivatives (acids, acid chlorides or esters) to afford the amide products 9.

Compounds 6, 8 and 9 are the key intermediate compounds in the formation of all other compounds disclosed within. Functionality of these key intermediates can be achieved by selection of the appropriate starting materials, or by halogenation, nitration, formylation, etc. and then further modified by the methods described within (e.g. Buchwald, Suzuki, Stille, aromatic substitution, etc.) to afford the desired entities 9 with the desired cis stereochemistry.

The compounds of the present invention possess at least two stereogenic carbon atoms and may therefore be obtained as pure enantiomers, as a mixture of enantiomers, or as a mixture of diastereoisomers. Generally these are isolated as a mixture of enantiomers. Diastereoisomers can be separated using straight phase or reversed phase chromatography. Methods for obtaining the pure enantiomers are well known in the art, e.g. chromatography using chiral columns.

Biological Activity:

Methods to determine receptor binding as well as in vitro and in vivo assays to determine biological activity of the compounds are well known. In general, the expressed receptor is treated with the compound to be tested and binding, stimulation or inhibition of a functional response is measured.

To measure binding, isolated cytosol containing the expressed GR may be used. Radioactive or fluorescence labelled compounds may also be used. As reference compound, native hormone or other compounds binding to the receptor can be used. As an alternative, also competition binding assays can be performed. These binding assays can be either developed in house or might be purchased as commercially available binding assays (kits). Experimental methods to determine binding affinities are well known in the art.

For selecting GR modulators, compounds should bind with an affinity of $<10^{-5}$ M to the receptor. More preferably, binding affinity is $<10^{-7}$ M and most preferably, binding affinity is $<10^{-8}$ M.

To measure a functional response, isolated DNA encoding the glucocorticoid receptor gene, preferably the human receptor, is expressed in suitable host cells, for instance in human osteoblastic U2OS cells.

Methods to construct recombinant glucocorticoid receptor-expressing cell lines are well known in the art. Expression of receptor is attained by expression of the DNA encoding the desired protein. Techniques for site directed mutagenesis, ligation of additional sequences, PCR and construction of suitable expression systems are all, by now, well known in the art. Portions or the entire DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts, such as bacteria, and eukaryotic hosts, such as yeast, plant cells, insect cells, mammalian cells, avian cells and the like.

In vitro, inflammation can be mimicked in a human cell line, stably transfected with human GR DNA that is stimulated to secrete cytokines, chemokines and other inflammatory mediators. Anti-inflammatory effects of compounds can be quantified by measuring inhibition of the inflammatory response in that cell line. By testing full dose response curves, $EC_{50}$ values can be calculated for both compounds and a reference compound like prednisolone. $EC_{50}$ values might be compared to the $EC_{50}$ values obtained for prednisolone within the same cellular assay. Preferably compounds have $EC_{50}$ values that are in the range of the $EC_{50}$ obtained for prednisolone. More preferably, $EC_{50}$ values are less than that obtained for prednisolone.

The skilled artisan will recognize that desirable $EC_{50}$ values are dependent on the compound tested. For example, a compound with an $EC_{50}$, which is less than $10^{-5}$ M is, generally, considered a candidate for drug selection. Preferably this value is lower than $10^{-7}$ M. However, a compound which has a higher $EC_{50}$, but is selective for the particular receptor, may be even a better candidate.

In vivo, the anti-inflammatory effect of compounds can be tested in mice that are treated with lipopolysaccharide (LPS). Compounds can be administered systemically at or before the time of LPS treatment. Anti-inflammatory effects can be quantified as an inhibition of LPS-induced TNFα in the serum of mice or any other inflammatory cytokine or chemokine (S. R. Hyde & R. E. McCallum, Infection and Immunity, 60; 976-982 (1992)). The potency to inhibit arthritis could be tested in the mouse collagen type II-induced arthritis model (CIA) as the ability to inhibit paw swelling (D. E. Trentham et al. J Exp Med 146; 857-868 (1977)), or another arthritis model.

The invention thus also resides in a pharmaceutical composition comprising a compound or a salt thereof having the general formula I. Thus, the compounds according to formula I can be used in therapy.

Suitable administration routes for the compounds of formula I or pharmaceutically acceptable salts thereof, also referred to herein as the active ingredient are intramuscular injections, subcutaneous injections, intravenous injections or intraperitoneal injections, oral and intranasal administration. Preferably, the compounds may be administered orally. The exact dose and regimen of administration of the active ingredient, or a pharmaceutical composition thereof, will necessarily be dependent upon the therapeutic effect to be achieved (e.g. treatment of asthma, R.A, I.B.D) and may vary with the particular compound, the route of administration, and the age and condition of the individual subject to whom the medicament is to be administered. Generally, a therapeutically effective daily dose is from about 0.001 mg to about 15 mg/kg of body weight per day per compound of the invention; preferably, from about 0.1 mg to about 10 mg/kg of body weight per day; and most preferably, from about 0.1 mg/kg to about 1.5 mg/kg of body weight per day. Some degree of routine dose optimization may be required to determine an optimal dosing level and pattern.

A further aspect of the invention resides in the use of the compounds according to Formula I or a pharmaceutically acceptable salt or solvate thereof for the preparation of a medicament for all indications wherein the glucocorticoid receptor need to be modulated i.e. within the fields of Rheumatology, Hematology, Pulmology, Dermatology, Gastro-enterology, Endocrinology, Neurology or Nephrology that are currently treated with steroidal glucocorticoids like prednisolone. Most preferred is the field of Rheumatology, in particular e.g. rheumatoid arthritis.

The compounds of the present invention thus modulate glucocorticoid receptor activity and they can be used in the treatment of immunological and inflammatory diseases. In particular the compounds can be used to treat rheumatic diseases such as rheumatoid arthritis, juvenile arthritis, and ankylosing spondylitis, dermatological diseases including psoriasis and pemphigus, allergic disorders including allergic rhinitis, atopic dermatitis, and contact dermatitis, pulmonary conditions including asthma and chronic obstructive pulmonary disease, and other immune and inflammatory diseases including Crohn disease, ulcerative colitis, systemic lupus erythematosus, autoimmune chronic active hepatitis, osteoarthritis, tendonitis, and bursitis. In addition, the compounds can be used to help prevent rejection of organs after organ transplantation.

More in particular the compounds can be used to treat rheumatoid arthritis, psoriasis, asthma and chronic obstructive pulmonary disease, Crohn disease or ulcerative colitis and the compounds can be used to help prevent rejection of organs after organ transplantation.

The compounds according to the invention can thus be used in the treatment of these diseases. i.e. all diseases wherein the patient is in need of modulating the glucocorticoid receptor.

EXAMPLES

Example 1

NB: The numbering in the examples refers to Scheme 1, where $R_1$, $R_3$, $R_4$, $R_6$-$R_9$=H, $R_{10}$=Me, $R_{11}$-$R_{14}$=H, unless stated otherwise.

Example 1, cis-2,2,2-trifluoro-N-(8-formyl-1,2,3,4,10,14b-hexahydro-10-methyl-dibenzo[b,f]pyrido[1,2-d][1,4]diazepin-2-yl)acetamide (9: $R_2$=C(O)CF$_3$; $R_8$=CHO)

A stirred solution of 2-bromonitrobenzene (1) (301 g, 1.5 mol) and N-methylaniline (176.5 g, 1.65 mol) in toluene (2.5 L) was degassed by bubbling through $N_2$ for 15 minutes. Caesium carbonate (537 g, 1.65 mol), Pd(OAc)$_2$ (973 mg, 4.3 mmol) and rac-BINAP (15.1 g, 24.3 mmol) were then added, with stirring, and the reaction was heated to 85° C. and held for 20 hours. Reaction was quenched with H$_2$O and the organics washed with 6M HCl, then H$_2$O and finally saturated brine then dried (Na$_2$SO$_4$). The organic layer was concentrated under reduced pressure and the crude product was purified by column chromatography on silica to afford (2) (341 g, 99%). Data: (m/z)=229 (M+H)$^+$.

To a stirred solution of (2) (100 g, 0.5 mol) in ethanol (1 L) was added SnCl$_2$.2H$_2$O (451 g, 2.0 mol) and the mixture was stirred at ambient temperature overnight. The ethanolic solution was split into 4 portions and each was poured into 6M NaOH solution in H$_2$O (1 L). This was stirred until the solution discoloured then the product was extracted into EtOAc. The organic layers were combined and washed with saturated brine then dried (Na$_2$SO$_4$). The organic layer was concentrated under reduced pressure and the crude product was purified by column chromatography on silica to afford (3) (78 g, 79%). Data: (m/z)=199 (M+H)$^+$.

A stirred solution of (3) (78 g, 0.39 mol) in formic acid (500 ml) was heated to reflux and held for 20 hours. The formic acid was removed under reduced pressure, and the resulting oil was dissolved in EtOAc. The organics were washed with NaHCO$_3$ solution in H$_2$O then H$_2$O and finally saturated brine then dried (Na$_2$SO$_4$). The organics were concentrated under reduced pressure and the crude product was purified by column chromatography on silica to afford (4) (61 g, 69%). Data: (m/z)=227 (M+H)$^+$.

To a stirred solution of (4) (61 g, 270 mmol) in DCM (500 ml) PCl$_5$ (56.3 g, 270 mmol) was added portionwise. The reaction mixture was stirred for 1 hour at ambient temperature then poured into NaHCO$_3$ solution in H$_2$O (1 L). The pH of the reaction mixture was adjusted using solid NaHCO$_3$ until it was basic to litmus paper. The organic layer was separated and concentrated under reduced pressure. The resulting oil was dissolved in Et$_2$O. A 6M HCl solution in H$_2$O was then added and the system stirred for 30 minutes. The aqueous layer was separated, the organics washed twice with 6M HCl solution in H$_2$O. The aqueous fractions were combined and washed with Et$_2$O then neutralised. The product was extracted into EtOAc and washed with saturated brine, dried (Na$_2$SO$_4$) and concentrated under reduced pressure. The crude product was purified by column chromatography on silica to afford (5) (30 g, 54%). Data: (m/z)=209 (M+H)$^+$.

A stirred solution of (5) (30 g, 144 mmol) in toluene (350 ml) was cooled to 0° C. then Danishefsky's diene (24.8 g, 144 mmol) and Yb(OTf)$_3$ (4.47 g, 7.2 mmol) were added. The solution was allowed to warm to ambient temperature and stir for 2 hours. The reaction was quenched with 0.1 M HCl in H$_2$O. Water was added and the product extracted into toluene. The organics were washed with saturated brine, dried (Na$_2$SO$_4$) then concentrated under reduced pressure to afford 10,14b-dihydro-10-methyl-dibenzo[b,f]pyrido[1,2-d][1,4]diazepin-2(1H)one, (47 g, crude). This compound was suspended in ethanol (1 L) then NaBH$_4$ (21.8 g, 576 mmol) was added and the reaction mixture was stirred for 8 hours at ambient temperature. The organics were partly evaporated under reduced pressure and the resulting slurry was poured into saturated NH$_4$Cl solution in H$_2$O and the product was extracted into EtOAc. The organics were washed with saturated brine, dried (Na$_2$SO$_4$) and concentrated under reduced pressure. The crude product was purified by column chromatography on silica to afford (6) (23.4 g, 58%). Data: (m/z)=281 (M+H)$^+$.

A stirred solution of (6) (10.0 g, 35.7 mmol) and triphenylphosphine (12.2 g, 46.4 mmol) in dry THF (150 ml) was cooled to 0° C. and diisopropylazodicarboxylate (9.2 ml, 46.4 mmol) was added dropwise. Diphenylphosphorylazide (10.0 ml, 46.4 mmol) was added dropwise, then the cooling was removed. The reaction was allowed to warm to ambient temperature and stirred for 2 hours. The reaction mixture was concentrated under reduced pressure and the crude product was purified by column chromatography on silica to afford (7) (13.1 g, 100%). Data: (m/z)=306 (M+H)$^+$.

To a stirred solution of (7) (10.9 g, 35.7 mmol) and triphenylphosphine (13.4 g, 51.1 mmol) in THF (150 ml) was added H$_2$O (2 ml). The reaction mixture was stirred for 24 hours at ambient temperature then concentrated under reduced pressure to afford (8) (35 g, crude). Data: (m/z)=280 (M+H)$^+$.

The crude material of (8) was taken up in MeOH (400 ml), with stirring, then triethylamine (19.4 ml, 140 mmol) and ethyltrifluoroacetate (20.9 ml, 175 mmol) were added and the reaction mixture was heated to 50° C. and held for 3 hours. The reaction mixture was concentrated under reduced pressure then purified by column chromatography on silica to afford cis-2,2,2-trifluoro-N-(1,2,3,4,10,14b-hexahydro-10-methyldibenzo[b,f]pyrido[1,2-d][1,4]diazepin-2-yl)acetamide (9: R$_2$=COCF$_3$) (5.7 g, 58% for two steps). Data: (m/z)=376 (M+H)$^+$.

Oxalyl chloride (436 µL, 5 mmol) was carefully added dropwise, with stirring, to DMF (0.5 ml) at 0° C. then held for 25 minutes. A solution of cis-2,2,2-trifluoro-N-(1,2,3,4,10,14b-hexahydro-10-methyldibenzo[b,f]pyrido[1,2-d][1,4]diazepin-2-yl)acetamide (9: R$_2$=COCF$_3$) (400 mg, 1.07 mmol) in DMF (2 ml) was added dropwise to the resulting suspension and the reaction mixture heated to 80° C. and held for 1.5 hours. The reaction was cooled to ambient temperature and quenched by dropwise addition of NaHCO$_3$ solution in H$_2$O. The product was extracted into EtOAc, dried (Na$_2$SO$_4$) and concentrated under reduced pressure. Then the crude product was purified by column chromatography on silica to afford cis-2,2,2-trifluoro-N-(8-formyl-1,2,3,4,10,14b-hexahydro-10-methyldibenzo[b,f]pyrido[1,2-d][1,4]diazepin-2-yl)acetamide (9: R$_2$=COCF$_3$; R$_8$=CHO) (130 mg, 30%). Data: (m/z)=404 (M+H)$^+$. [Column chromatography also afforded cis-2,2,2-trifluoro-N-(6-formyl-1,2,3,4,10,14b-hexahydro-10-methyldibenzo[b,f]pyrido[1,2-d][1,4]diazepin-2-yl)acetamide (9: R$_2$=COCF$_3$; R$_6$=CHO) (45 mg, 10%). Data: (m/z)=404 (M+H)$^+$.]

Example 2, cis-2,2,2-trifluoro-N-(1,2,3,4,10,14b-hexahydro-10-methyl-8-nitrodibenzo[b,f]pyrido[1,2-d][1,4]diazepin-2-yl)acetamide (9: R$_2$=COCF$_3$; R$_8$=NO$_2$)

A stirred solution of TFAA (188 µL, 1.33 mmol) and TBAN (406 mg, 1.33 mmol) in DCM (5 ml) was cooled to 0° C. and stirred for 20 minutes then added dropwise to a solution of (9: R$_2$=COCF$_3$) (250 mg, 0.67 mmol) in DCM (5 ml). The reaction mixture was stirred for 1.5 hours at 0° C. then quenched (at 0° C.) with NaHCO$_3$ solution in H$_2$O. The organics were separated and washed with H$_2$O then saturated brine, then were dried (PE-filter) and concentrated under reduced pressure. The crude product was purified by column chromatography on silica to afford cis-2,2,2-trifluoro-N-(1,2,3,4,10,14b-hexahydro-10-methyl-8-nitrodibenzo[b,f]pyrido[1,2-d][1,4]diazepin-2-yl)acetamide (9: R$_2$=COCF$_3$; R$_8$=NO$_2$) (110 mg, 42%). Data: (m/z)=421 (M+H)$^+$.

Example 3, cis-N-(8-cyano-1,2,3,4,10,14b-hexahydro-10-methyldibenzo[b,f]pyrido[1,2-d][1,4]diazepin-2-yl)-2,2,2-trifluoroacetamide (9: R$_2$=COCF$_3$; R$_8$=CN)

A stirred solution of (6) (12.7 g, 45.4 mmol) in acetone (175 ml) was cooled to 0° C. and N-bromosuccinimide (10.4 g, 58.4 mmol) was added portionwise. The solution was allowed to warm to ambient temperature and stir for 3 hours. The reaction was then quenched with NaHCO$_3$ solution in H$_2$O and the product was extracted into EtOAc. The organics were washed with saturated brine, dried (Na$_2$SO$_4$) and concentrated under reduced pressure. The crude product was purified by column chromatography on silica to afford (6: R$_8$=Br) (11.0 g, 67%). Data: (m/z)=360 (M+H)$^+$.

(7: R$_8$=Br). This compound was prepared, in an analogous manner as described in Example 1 (vide infra). Product was not purified and thus carried through to next step crude. Data: (m/z)=385 (M+H)$^+$.

(9: R$_2$=COCF$_3$; R$_8$=Br) This compound was prepared, in an analogous manner as described in Example 1 (35% for three steps). Data: (m/z)=455 (M+H)$^+$.

A solution of (9: R$_2$=COCF$_3$; R$_8$=Br) (2 g, 4.4 mmol) and CuCN (1 g, 11 mmol) was degassed by bubbling nitrogen through for 0.5 hours. The reaction mixture was then heated to 200° C. and held for 4 hours, with stirring. The reaction was then quenched with NH$_4$OH solution in H$_2$O then filtered. The product was extracted into EtOAc and the organics were washed with H$_2$O then dried (Na$_2$SO$_4$). The organics were concentrated under reduced pressure and the crude product purified by column chromatography on silica to afford cis-N-(8-cyano-1,2,3,4,10,14b-hexahydro-10-methyldibenzo[b,f]pyrido[1,2-d][1,4]diazepin-2-yl)-2,2,2-trifluoroacetamide (9: R$_2$=COCF$_3$; R$_8$=CN) (1.1 g, 62%). Data: (m/z)=401 (M+H)$^+$.

Example 4, cis-1,2,3,4,10,14b-hexahydro-10-methyl-N-phenyl-2-(2,2,2-trifluoroacetylamino)dibenzo[b,f]pyrido[1,2-d][1,4]diazepine-8-carboxamide (9: R$_2$=COCF$_3$; R$_8$=C$_7$N$_6$NO)

To a stirred solution of cis-N-(8-cyano-1,2,3,4,10,14b-hexahydro-10-methyldibenzo-[b,f]pyrido[1,2-d][1,4]diazepin-2-yl)-2,2,2-trifluoroacetamide (9: R$_2$=COCF$_3$; R$_8$=CN) (900 mg, 2.25 mmol) in EtOH (50 ml) was added 6N KOH (20 ml). The reaction mixture was heated to 120° C. and held for 1.5 hours using a microwave (120W). The reaction mixture was cooled to ambient temperature and neutralised with 2M HCl in H$_2$O and the solvents removed by freeze-drying. The crude product was taken up in MeOH (50 ml) then triethylamine (1.5 ml, 10.8 mmol) and ethyl trifluoroacetate (1.4 ml, 11.7 mmol) were added. The reaction mixture was heated to 50° C. and held for 3 hours then cooled to ambient temperature. The product was isolated by an acid-base extraction and the organic layer was washed with H$_2$O, then saturated brine, then dried (Na$_2$SO$_4$) and concentrated under reduced pressure to afford crude (9: R$_2$=COCF$_3$; R$_8$=CO$_2$H) (737 mg, 78% for 2 steps). Data: (m/z)=420 (M+H)$^+$.

To a stirred solution of (9: R$_2$=COCF$_3$; R$_8$=CO$_2$H) (30 mg, 0.72 mmol) in DMF (1 ml) was added TBTU (34.5 mg, 0.108 mmol) and DIPEA (68.3 µL, 0.360 mmol) and the mixture was stirred for 10 minutes. Aniline (7.2 µL, 0.792 mmol) was then added and the reaction mixture was stirred at ambient temperature for 70 hours. The reaction was quenched with Na$_2$CO$_3$ solution in H$_2$O and the product was extracted into DCM. The organic layer was dried (Na$_2$SO$_4$) and concentrated under reduced pressure then the crude product was purified by column chromatography to afford cis-1,2,3,4,10,14b-hexahydro-10-methyl-N-phenyl-2-(2,2,2-trifluoroacetylamino)dibenzo[b,f]pyrido[1,2-d][1,4]diazepine-8-carboxamide (9: $R_2$=COCF$_3$; $R_8$=C$_7$H$_6$NO) (25 mg, 70%). Data: (m/z)=495 (M+H)$^+$.

Example 5, cis-2,2-dichloro-N-(8-cyano-1,2,3,4,10,14b-hexahydro-10-methyldibenzo-[b,f]pyrido[1,2-d][1,4]diazepin-2-yl)acetamide (9: $R_2$=COCCl$_2$; $R_8$=CN)

To a stirred solution of cis-N-(8-cyano-1,2,3,4,10,14b-hexahydro-10-methyldibenzo-[b,f]pyrido[1,2-d][1,4]diazepin-2-yl)-2,2,2-trifluoroacetamide (9: $R_2$=COCF$_3$; $R_8$=CN) (900 mg, 2.25 mmol) in EtOH (50 ml) was added 2N NaOH (12 ml). The reaction mixture was stirred at ambient temperature for 3 hours then the product was isolated by an acid-base extraction and the organic layer was washed with H$_2$O then saturated brine, then dried (Na$_2$SO$_4$) and concentrated under reduced pressure to afford crude (8: $R_8$=CN) (687 mg, 100%). Data: (m/z)=305 (M+H)$^+$.

A stirred solution of (8: $R_8$=CN) (20 mg, 0.066 mmol) and triethylamine (5.75 μL, 0.069 mmol) in DCM (0.5 ml) was cooled to 0° C. then a solution of dichloroacetyl chloride (6 μL, 0.069 mmol) was added dropwise. The reaction was stirred for 2 hours then quenched with Na$_2$CO$_3$ solution in H$_2$O and the product was extracted into DCM. The organic layer was dried (Na$_2$SO$_4$) and concentrated under reduced pressure then the crude product was purified by column chromatography to afford cis-2,2-dichloro-N-(8-cyano-1,2,3,4,10,14b-hexahydro-10-methyldibenzo[b,f]pyrido[1,2-d][1,4]diazepin-2-yl)acetamide (9: $R_2$=COCCl$_2$; $R_8$=CN) (20 mg, 81%). Data: (m/z)=415 (M+H)$^+$.

Example 6, cis-N-[1,2,3,4,10,14b-hexahydro-10-methyl-N-(2,2,2-trifluoroacetylamino)dibenzo[b,f]pyrido[1,2-d][1,4]diazepin-8-yl]-2-methylpropanamide (9: $R_2$=COCF$_3$; $R_8$=C$_4$H$_8$NO)

To a stirred solution of (9: $R_2$=COCF$_3$; $R_8$=Br) (5.16 g, 11.36 mmol), Pd$_2$(dba)$_3$ (0.1 g), 2-(di-t-butylphosphino)biphenyl (0.2 g) and NaOBu$^t$ (2.18 g, 22.7 mmol) in DME (150 ml) was added benzylamine (2.48 ml, 22.7 mmol) and the reaction mixture was heated to 75° C. and held for 20 hours. The reaction mixture was cooled to ambient temperature and was quenched by the addition of EtOAc and NaHCO$_3$ solution in H$_2$O. The organics were separated and washed with H$_2$O then saturated brine, then dried (Na$_2$SO$_4$) and concentrated under reduced pressure. The crude product was purified by column chromatography to afford (9: $R_2$=COCF$_3$; $R_8$=C$_7$H$_8$N) (4.51 g, 83%). Data: (m/z)=481 (M+H)$^+$.

To a stirred solution of (9: $R_2$=COCF$_3$; $R_8$=C$_7$H$_8$N) (2.00 g, 4.16 mmol) in EtOH (35 ml) was added 10% Pd/C (0.2 ml, 22.7 mmol) and HCl in dioxane (1 ml) and the reaction mixture was purged three times with nitrogen. The reaction mixture was stirred for 20 hours under Hydrogen (2 bar). The reaction was quenched by the addition of EtOAc and NaHCO$_3$ solution in H$_2$O and was filtered (celite). The organics were separated and washed with H$_2$O then saturated brine, then dried (Na$_2$SO$_4$) and concentrated under reduced pressure. The crude product was purified by column chromatography on silica to afford (9: $R_2$=COCF$_3$; $R_8$=NH$_2$) (1.39 g, 86%). Data: (m/z)=391 (M+H)$^+$.

A stirred solution of (9: $R_2$=COCF$_3$; $R_8$=NH$_2$) (250 mg, 0.643 mmol) and triethylamine (95 μL, 0.675 mmol) in DCM (7.5 ml) was cooled to 0° C. and a solution of isobutyrylchloride (70 μL, 0.675 mmol) was added dropwise. The reaction was stirred at 0° C. for 1 hour then quenched by the addition of EtOAc and NaHCO$_3$ solution in H$_2$O. The organics were separated and washed with H$_2$O then saturated brine, then dried (Na$_2$SO$_4$) and concentrated under reduced pressure. The crude product was purified by column chromatography on silica to afford cis-N-[1,2,3,4,10,14b-hexahydro-10-methyl-N-(2,2,2-trifluoroacetylamino)dibenzo[b,f]pyrido[1,2-d][1,4]diazepin-8-yl]-2-methylpropanamide (9: $R_2$=COCF$_3$; $R_8$=C$_4$H$_8$NO) (208 mg, 70%). Data: (m/z)=461 (M+H)$^+$.

Example 7, cis-N-[1,2,3,4,10,14b-hexahydro-10-methyl-N-phenyl-2-(2,2,2-trifluoroacetylamino)dibenzo[b,f]pyrido[1,2-d][1,4]diazepin-8-yl]-4-methyl-1,2,3-thiadiazole-5-carboxamide (9: $R_2$=COCF$_3$; $R_8$=C$_4$H$_4$N$_3$OS)

This compound was prepared, in an analogous manner as described in Example 6, from (9: $R_2$=COCF$_3$; $R_8$=NH$_2$), to afford, cis-N-[1,2,3,4,10,14b-hexahydro-10-methyl-N-phenyl-2-(2,2,2-trifluoroacetylamino)dibenzo[b,f]pyrido[1,2-d][1,4]diazepin-8-yl]-4-methyl-1,2,3-thiadiazole-5-carboxamide (9: $R_2$=COCF$_3$; $R_8$=C$_4$H$_4$N$_3$OS) (43%). Data: (m/z)=517 (M+H)$^+$.

Example 8, ethyl cis-1,2,3,4,10,14b-hexahydro-10-methyl-2-(2,2,2-trifluoroacetylamino)dibenzo[b,f]pyrido[1,2-d][1,4]diazepine-8-carboxylate (9: $R_2$=COCF$_3$; $R_8$=C$_3$H$_5$O$_2$)

A stirred solution of (9: $R_2$=COCF$_3$; $R_8$=Br) (500 mg, 1.10 mmol) in dry THF (10 ml) was cooled to −75° C. and n-BuLi (1.44 ml 2.10 mmol) was added dropwise. After 5 minutes ethyl chloroformate (525 μL, 5.50 mmol) was added dropwise and the reaction was stirred at −75° C. for 1.5 hours. The reaction was quenched by dropwise addition of H$_2$O and the product was extracted into EtOAc. The organic layer was dried (Na$_2$SO$_4$) and concentrated under reduced pressure. The crude product was purified by column chromatography on silica to afford ethyl cis-1,2,3,4,10,14b-hexahydro-10-methyl-2-(2,2,2-trifluoroacetylamino)dibenzo[b,f]pyrido[1,2-d][1,4]diazepine-8-carboxylate (9: $R_2$=COCF$_3$; $R_8$=C$_3$H$_5$O$_2$) (75 mg, 15%). Data: (m/z)=448 (M+H)$^+$.

Example 9, cis-N-(7-chloro-8-cyano-1,2,3,4,10,14b-hexahydro-10-methyl-dibenzo-[b,f]pyrido[1,2-d][1,4]diazepin-2-yl)-2,2,2-trifluoroacetamide (9: $R_2$=COCF$_3$; $R_7$=Cl; $R_8$=CN)

This compound was prepared, in an analogous manner as described in Example 3, from (8: $R_7$=Cl; $R_8$=Br) to afford cis-N-(7-chloro-8-cyano-1,2,3,4,10,14b-hexahydro-10-methyl-dibenzo[b,f]pyrido[1,2-d][1,4]diazepin-2-yl)-2,2,2-trifluoroacetamide (9: $R_2$=COCF$_3$; $R_7$=Cl; $R_8$=CN) (40%). Data: (m/z)=435 (M+H)$^+$.

Example 10, cis-2,2,2-trifluoro-N-(1,2,3,4,10,14b-hexahydro-10,14-dimethyl-8-nitrodibenzo[b,f]pyrido[1,2-d][1,4]diazepin-2-yl)-acetamide (9: $R_2$=COCF$_3$; $R_8$=NO$_2$; $R_{14}$=CH$_3$)

This compound was prepared, in an analogous manner as described in Example 2, from (9: $R_2$=COCF$_3$; $R_{14}$=CH$_3$), to afford cis-2,2,2-trifluoro-N-(1,2,3,4,10,14b-hexahydro-10,14-dimethyl-8-nitro-dibenzo[b,f]pyrido[1,2-d][1,4]diazepin-2-yl)-acetamide (9: $R_2$=COCF$_3$; $R_8$=NO$_2$; $R_{14}$=CH$_3$) (59%). Data: (m/z)=435 (M+H)$^+$.

Example 11, cis-N-(14-bromo-1,2,3,4,10,14b-hexahydro-10-methyl-8-nitro-dibenzo-[b,f]pyrido[1,2-d][1,4]diazepin-2-yl)-2,2,2-trifluoroacetamide (9: $R_2$=COCF$_3$; $R_8$=NO$_2$; $R_{14}$=Br)

This compound was prepared, in the analogous manner as described in Example 2, from (9: $R_2$=COCF$_3$; $R_{14}$=Br), to afford cis-N-(14-bromo-1,2,3,4,10,14b-hexahydro-10-methyl-8-nitro-dibenzo[b,f]pyrido[1,2-d][1,4]diazepin-2-yl)-2,2,2-trifluoroacetamide (9: $R_2$=COCF$_3$; $R_8$=NO$_2$; $R_{14}$=Br) (45%). Data: (m/z)=500 (M+H)$^+$.

Example 12, cis-2,2,2-trifluoro-N-[1,2,3,4,10,14b-hexahydro-10-methyl-8-nitro-14-(pyridine-2-yl)-dibenzo[b,f]pyrido[1,2-d][1,4]diazepin-2-yl]acetamide (9: $R_2$=COCF$_3$; $R_8$=NO$_2$; $R_{14}$=2-C$_5$H$_4$N)

To a stirred solution of (9: $R_2$=COCF$_3$; $R_8$=NO$_2$; $R_{14}$=Br) (40 mg, 0.080 mmol) in toluene (3 ml) was charged PdCl$_2$(PPh$_3$)$_2$ (3.5 mg, 0.005 mmol), copper iodide (8.0 mg, 0.005 mmol), caesium fluoride (24 mg, 0.160 mmol) and 2-(tributylstannyl)pyridine (44 mg, 0.120 mmol). The reaction mixture was heated to 120° C. and held for 24 hours. The reaction was quenched with NaHCO$_3$ solution in H$_2$O and the product was extracted into EtOAc. The organics were washed with H$_2$O then saturated brine, then dried (Na$_2$SO$_4$) and concentrated under reduced pressure. The crude product was purified by column chromatography on silica to afford cis-2,2,2-trifluoro-N-[1,2,3,4,10,14b-hexahydro-10-methyl-8-nitro-14-(pyridine-2-yl)-dibenzo[b,f]pyrido[1,2-d][1,4]diazepin-2-yl]acetamide (9: $R_2$=COCF$_3$; $R_8$=NO$_2$; $R_{14}$=2-C$_5$H$_4$N) (8 mg, 20%). Data: (m/z)=498 (M+H)$^+$.

Example 13, cis-N-(8,14-dicyano-1,2,3,4,10,14b-hexahydro-10-methyldibenzo[b,f]-pyrido[1,2-d][1,4]diazepin-2-yl)-2,2,2-trifluoroacetamide (9, $R_2$=COCF$_3$; $R_8$=CN; $R_{14}$=CN)

This compound was prepared, in an analogous manner as described in Example 3, from (9: $R_2$=COCF$_3$; $R_8$=Br; $R_{14}$=Br), to afford cis-N-(8,14-dicyano-1,2,3,4,10,14b-hexahydro-10-methyldibenzo[b,f]pyrido[1,2-d][1,4]diazepin-2-yl)-2,2,2-trifluoroacetamide (9: $R_2$=COCF$_3$; $R_8$=CN; $R_{14}$=CN) (74%). Data: (m/z)=426 (M+H)$^+$.

Example 14, (2α,4α,14bα)-2,2,2-trifluoro-N-[1,2,3,4,10,14b-hexahydro-4,10-dimethyl-8-(pyridin-4-yl)dibenzo[b,f]pyrido[1,2-d][1,4]diazepin-2-yl]acetamide (9: $R_2$=CO—CF$_3$; $R_4$=CH$_3$; $R_8$=4-C$_5$H$_4$N)

A stirred solution of (9: $R_2$=COCF$_3$; $R_4$=CH$_3$; $R_8$=Br) (405 mg, 0.865 mmol), PdCl$_2$(PPh$_3$)$_2$ (18.2 mg, 0.026 mmol), K$_3$PO$_4$.7H$_2$O (342.6 mg, 0.101 mmol), AsPh$_3$ (17.7 mg, 0.058 mmol) and 2,2-dimethylpropanediol cyclic ester pyridine-4-boronic acid (456 mg, 2.38 mmol) in 1:6 mixture of water:dioxane (3.5 ml) was heated at 30 Watt to 150° C. in the microwave for 15 minutes. The reaction was quenched with NaHCO$_3$ solution in H$_2$O and the product was extracted into DCM. The organics were washed with water and concentrated under reduced pressure. The crude product was purified by column chromatography on silica to afford (2α,4α,14bα)-2,2,2-trifluoro-N-[1,2,3,4,10,14b-hexahydro-4,10-dimethyl-8-(pyridin-4-yl)dibenzo[b,f]pyrido[1,2-d][1,4]diazepin-2-yl]acetamide (9: $R_2$=COCF$_3$; $R_4$=CH$_3$; $R_8$=4-C$_5$H$_4$N)

(9: $R_2$=COCF$_3$; $R_4$=CH$_3$; $R_8$=4-C$_5$H$_4$N) (342 mg, 85%). Data: (m/z)=467 (M+H)$^+$.

Example 15, cis-N-(1,2,3,4,10,14b-hexahydro-10-methyl-8-nitrodibenzo[b,f]pyrido-[1,2-d][1,4]diazepin-2-yl)-2-thiophenethanamide (9: $R_2$=COC$_5$H$_5$S; $R_8$=NO$_2$)

This compound was prepared, in an analogous manner as described in Example 4, from (8: $R_8$=NO$_2$), to cis-N-(1,2,3,4,10,14b-hexahydro-10-methyl-8-nitrodibenzo[b,f]-pyrido[1,2-d][1,4]diazepin-2-yl)-2-thiophenethanamide (9: $R_2$=COC$_5$H$_5$S; $R_8$=NO$_2$) (75%). Data: (m/z)=449 (M+H)$^+$.

Example 16, cis-N-(7-chloro-1,2,3,4,10,14b-hexahydro-4,10-dimethyldibenzo[b,f]-pyrido[1,2-d][1,4]diazepin-2-yl)-2,2-difluoroacetamide (9: $R_2$=COCHF$_2$; $R_4$=CH$_3$; $R_7$=Cl)

This compound was prepared, in an analogous manner as described in Example 4, from (8, $R_4$=CH$_3$$R_7$=Cl), to afford cis-N-(7-chloro-1,2,3,4,10,14b-hexahydro-4,10-dimethyldibenzo[b,f]pyrido[1,2-d][1,4]diazepin-2-yl)-2,2-difluoroacetamide (9: $R_2$=COCHF$_2$; $R_4$=CH$_3$; $R_7$=Cl) (71%). Data: (m/z)=406 (M+H)$^+$.

Example 17, cis-N-(1,2,3,4,10,14b-hexahydro-10-methyl-8-nitro-dibenzo[b,f]-pyrido[1,2-d][1,4]diazepin-2-yl)-N',N'-dimethylurea (9: $R_2$=COC$_2$H$_6$N; $R_8$=NO$_2$)

This compound was prepared, in an analogous manner as described in Example 5, from (8, $R_8$=NO$_2$), to afford cis-N-(1,2,3,4,10,14b-hexahydro-10-methyl-8-nitro-dibenzo-[b,f]pyrido[1,2-d][1,4]diazepin-2-yl)-N',N'-dimethylurea (9: $R_2$=COC$_2$H$_6$N; $R_8$=NO$_2$) (54%). Data: (m/z)=396 (M+H)$^+$.

Example 18, cis-2,2,2-trifluoro-N-[1,2,3,4,10,14b-hexahydro-8-[(1-(hydroxyimino)-ethyl]-10,14-dimethyldibenzo[b,f]pyrido[1,2-d][1,4]diazepin-2-yl]acetamide (9: $R_2$=COCF$_3$; $R_8$=2-C$_2$H$_4$NO; $R_{14}$=CH$_3$)

A solution of (9: $R_2$=COCF$_3$; $R_8$=C$_2$H$_3$O; $R_{14}$=CH$_3$, Example 21) (50 mg, 0.116 mmol), hydroxylamine.HCl (12 mg, 0.174 mmol) and triethylamine (1 drop) in THF (1 ml) was heated to 50° C. and held for 20 hours. NaHCO$_3$ solution in H$_2$O was added and the product extracted into EtOAc. The organics were washed with H$_2$O, then saturated brine, then dried (Na$_2$SO$_4$). The organics were concentrated under reduced pressure and the crude product was purified by column chromatography on silica to afford cis-2,2,2-trifluoro-N-[1,2,3,4,10,14b-hexahydro-8-[1-(hydroxylimino)ethyl]-10,14-dimethyldibenzo[b,f]pyrido[1,2-d][1,4]diazepin-2-yl]acetamide (9: $R_2$=CO—CF$_3$; $R_8$=2-C$_2$H$_4$NO; $R_{14}$=CH$_3$) (49 mg, 94%). Data: (m/z)=447 (M+H)$^+$.

Example 19, cis-N-(1,2,3,4,10,14b-hexahydro-10-methyl-8-nitro-dibenzo[b,f]pyrido[1,2-d][1,4]diazepin-2-yl)-furan-3-carboxamide (9: $R_2$=COC$_4$H$_3$O; $R_8$=NO$_2$)

This compound was prepared, in an analogous manner as described in Example 5, from (8: $R_8$=NO$_2$), to afford cis-N-(1,2,3,4,10,14b-hexahydro-10-methyl-8-nitro-dibenzo[b,f]pyrido[1,2-d][1,4]diazepin-2-yl)-furan-3-carboxamide (9: $R_2$=COC$_4$H$_3$O; $R_8$=NO$_2$) (45%). Data: (m/z)=419 (M+H)$^+$.

Example 20, cis-2,2,2-trifluoro-N-[1,2,3,4,10,14b-hexahydro-10-methyl-8-(pyridin-4-yl)dibenzo[b,f]pyrido[1,2-d][1,4]diazepin-2-yl]acetamide (9: $R_2$=COCF$_3$; $R_8$=4-C$_5$H$_4$N)

This compound was prepared, in an analogous manner as described in Example 5, from (8: $R_8$=4-C$_5$H$_4$N), to afford cis-2,2,2-trifluoro-N-[1,2,3,4,10,14b-hexahydro-10-methyl-8-(pyridin-4-yl)dibenzo[b,f]pyrido[1,2-d][1,4]diazepin-2-yl]acetamide (9: $R_2$=COCF$_3$; $R_8$=4-C$_5$H$_4$N) (31%). Data: (m/z)=481 (M+H)$^+$.

Example 21, cis-N-(8-acetyl-1,2,3,4,10,14b-hexahydro-10,14-dimethyldibenzo[b,f]-pyrido[1,2-d][1,4]diazepin-2-yl)-2,2,2-trifluoroacetamide (9: $R_2$=COCF$_3$; $R_8$=C$_2$H$_3$O; $R_{14}$=CH$_3$)

This compound was prepared, in an analogous manner as described in Example 12, from (9: $R_2$=COCF$_3$; $R_8$=Br; $R_{14}$=CH$_3$), to afford cis-N-(8-acetyl-1,2,3,4,10,14b-hexahydro-10,14-dimethyldibenzo[b,f]pyrido[1,2-d][1,4]diazepin-2-yl)-2,2,2-trifluoroacetamide (9: $R_2$=COCF$_3$; $R_8$=C$_2$H$_3$O; $R_{14}$=CH$_3$) (22%). Data: (m/z)=432 (M+H)$^+$.

Example 22, cis-N-(1,2,3,4,10,14b-hexahydro-10-methyl-8-nitrodibenzo[b,f]pyrido-[1,2-d][1,4]diazepin-2-yl)-2-(methylthio)acetamide (9: $R_2$=COC$_2$H$_5$S; $R_8$=NO$_2$)

This compound was prepared, in an analogous manner as described in Example 4, from (8, $R_8$=NO$_2$), to afford cis-N-(1,2,3,4,10,14b-hexahydro-10-methyl-8-nitrodibenzo[b,f]pyrido[1,2-d][1,4]diazepin-2-yl)-2-(methylthio)acetamide (9: $R_2$=COC$_2$H$_5$S; $R_8$=NO$_2$) (25%). Data: (m/z)=413 (M+H)$^+$.

Example 23, cis-2,2,2-trifluoro-N-[1,2,3,4,10,14b-hexahydro-10,14-dimethyl-8-(pyramidin-2-yl)dibenzo[b,f]pyrido[1,2-d][1,4]diazepin-2-yl]acetamide (9: $R_2$=COCF$_3$; $R_8$=C$_4$H$_3$N$_2$; $R_{14}$=CH$_3$)

This compound was prepared, in an analogous manner as described in Example 12, from (9: $R_2$=COCF$_3$; $R_8$=Br; $R_{14}$=CH$_3$), to afford cis-2,2,2-trifluoro-N-[1,2,3,4,10,14b-hexahydro-10,14-dimethyl-8-(pyrimidin-2-yl)dibenzo[b,f]pyrido[1,2-d][1,4]diazepin-2-yl]acetamide (9: $R_2$=COCF$_3$; $R_8$=C$_4$H$_3$N$_2$; $R_{14}$=CH$_3$) (14%). Data: (m/z)=468 (M+H)$^+$.

Example 24, cis-N-(1,2,3,4,10,14b-hexahydro-10-methyl-8-nitrodibenzo[b,f]pyrido-[1,2-d][1,4]diazepin-2-yl)propionamide (9, $R_2$=$COC_2H_5$; $R_8$=$NO_2$)

This compound was prepared, in an analogous manner as described in Example 5, from (8: $R_8$=$NO_2$), to afford cis-N-(1,2,3,4,10,14b-hexahydro-10-methyl-8-nitrodibenzo[b,f]pyrido[1,2-d][1,4]diazepin-2-yl)propionamide (9, $R_2$=$COC_2H_5$; $R_8$=$NO_2$) (55%). Data: (m/z)=381 (M+H)$^+$.

Example 25, (2α,4α,14bα)-2,2,2-trifluoro-N-(8-fluoro-1,2,3,4,10,14b-hexahydro-4,10-dimethyldibenzo[b,f]pyrido[1,2-d][1,4]diazepin-2-yl)acetamide (9: $R_2$=$COCF_3$; $R_4$=$CH_3$; $R_8$=F)

This compound was prepared, in an analogous manner as described in Example 1, from (8: $R_4$=$CH_3$; $R_8$=F), to afford (2α,4α,14bα)-2,2,2-trifluoro-N-(8-fluoro-1,2,3,4,-10,14b-hexahydro-4,10-dimethyldibenzo[b,f]pyrido[1,2-d][1,4]diazepin-2-yl)acetamide (9: $R_2$=$COCF_3$; $R_4$=$CH_3$; $R_8$=F) (62%). Data: (m/z)=408 (M+H)$^+$.

Example 26, cis-N-(1,2,3,4,10,14b-hexahydro-10-methyl-8-nitrodibenzo[b,f]pyrido-[1,2-d][1,4]diazepin-2-yl)-2-methoxyacetamide (9: $R_2$=$COC_2H_5O$; $R_8$=$NO_2$)

This compound was prepared, in an analogous manner as described in Example 5, from (8: $R_8$=$NO_2$), to afford, cis-N-(1,2,3,4,10,14b-hexahydro-10-methyl-8-nitrodibenzo[b,f]pyrido[1,2-d][1,4]diazepin-2-yl)-2-methoxyacetamide (9: $R_2$=$COC_2H_5O$; $R_8$=$NO_2$) (46%). Data: (m/z)=397 (M+H)$^+$.

Example 27, cis-2,2,2-trifluoro-N-(1,2,3,4,10,14b-hexahydro-10-methyl-8-(2-methyl-2H-tetrazol-5-yl)dibenzo[b,f]pyrido[1,2-d][1,4]diazepin-2-yl)acetamide (9: $R_2$=$COCF_3$; $R_8$=$C_2H_3N_4$)

To a stirred solution of (9: $R_2$=$COCF_3$; $R_8$=CN, Example 3) (100 mg, 0.250 mmol) in DMF (2.5 ml) was charged sodium azide (195 mg, 3.00 mmol) and ammonium chloride (160 mg 3.00 mmol). The reaction mixture was heated at 20 Watt to 150° C. in the microwave and held for 5 minutes. An acid-base extraction was performed and the product extracted into EtOAc. The organic layer was washed with water, dried ($Na_2SO_4$) and concentrated under reduced pressure to yield a solid (48 mg, 43%). The crude product (39 mg, 0.088 mmol) was dissolved in 1:1 mixture of DMF:acetone (5 ml) then sodium bicarbonate (11.1 mg, 0.132 mmol) and methyl iodide (54.7 mg, 0.880 mmol) were added and the reaction mixture was stirred at ambient temperature for 24 hours. EtOAc was then added and the reaction mixture was washed with water, dried ($Na_2SO_4$) then concentrated under reduced pressure. The crude product was purified by column chromatography over silica to afford cis-2,2,2-trifluoro-N-(1,2,3,4,10,14b-hexahydro-10-methyl-8-(2-methyl-2H-tetrazol-5-yl)dibenzo[b,f]pyrido[1,2-d][1,4]diazepin-2-yl)acetamide (9: $R_2$=$COCF_3$; $R_8$=$C_2H_3N_4$) (7 mg, 17%). Data: (m/z)=458 (M+H)$^+$.

Example 28, cis-2,2,2-trifluoro-N-(1,2,3,4,10,14b-hexahydro-8-[(hydroxyimino)-ethyl]-10-methyldibenzo[b,f]pyrido[1,2-d][1,4]diazepin-2-yl)acetamide (9: $R_2$=$COCF_3$; $R_8$=$C_2H_4NO$)

This compound was prepared, in an analogous manner as described in Example 18, from (9: $R_2$=$COCF_3$; $R_8$=$COCH_3$), to afford cis-2,2,2-trifluoro-N-(1,2,3,4,10,14b-hexahydro-8-[(hydroxyimino)ethyl]-10-methyldibenzo[b,f]pyrido[1,2-d][1,4]diazepin-2-yl)acetamide (9: $R_2$=$COCF_3$; $R_8$=$C_2H_4NO$) (55%). Data: (m/z)=433 (M+H)$^+$.

Example 29, (2α,4α,14bα)-N-(7-chloro-1,2,3,4,10,14b-hexahydro-4,10-dimethyldibenzo[b,f]pyrido[1,2-d][1,4]diazepin-2-yl)-3,5-dimethylisoxazole-4-carboxamide (9: $R_2$=$COC_5H_6NO$; $R_4$=$CH_3$; $R_7$=Cl)

This compound was prepared, in an analogous manner as described in Example 5, from (8: $R_4$=$CH_3$; $R_7$=Cl), to afford (2α,4α,14bα)-N-(7-chloro-1,2,3,4,10,14b-hexahydro-4,10-dimethyl-dibenzo[b,f]pyrido[1,2-d][1,4]diazepin-2-yl)-3,5-dimethylisoxazole-4-carboxamide (9: $R_2$=$COC_5H_6NO$; $R_4$=$CH_3$; $R_7$=Cl) (15%). Data: (m/z)=451 (M+H)$^+$.

Example 30, cis-N-(1,2,3,4,10,14b-hexahydro-10-methyl-8-nitrodibenzo[b,f]pyrido-[1,2-d][1,4]diazepin-2-yl)-5-methylisoxazole-4-carboxamide (9: $R_2$=$COC_4H_4NO$; $R_8$=$NO_2$)

This compound was prepared, in an analogous manner as described in Example 4, from (8, $R_8$=$NO_2$), to afford cis-N-(1,2,3,4,10,14b-hexahydro-10-methyl-8-nitrodibenzo-[b,f]pyrido[1,2-d][1,4]diazepin-2-yl)-5-methylisoxazole-4-carboxamide (9: $R_2$=CO—$C_4H_4NO$; $R_8$=$NO_2$) (27%). Data: (m/z)=434 (M+H)$^+$.

Example 31, cis-N-(1,2,3,4,10,14b-hexahydro-10-methyl-8-nitrodibenzo[b,f]pyrido[1,2-d][1,4]diazepin-2-yl)-4-methyl-1,2,3-thiadiazole-5-carboxamide (9: $R_2$=$COC_3H_3N_2S$; $R_8$=$NO_2$)

This compound was prepared, in an analogous manner as described in Example 5, (8: $R_8$=$NO_2$), to afford cis-N-(-1,2,3,4,10,14b-hexahydro-10-methyl-8-nitrodibenzo-[b,f]pyrido[1,2-d][1,4]diazepin-2-yl)-4-methyl-1,2,3-thiadiazole-5-carboxamide (9: $R_2$=$COC_3H_3N_2S$; $R_8$=$NO_2$) (72%). Data: (m/z)=451 (M+H)$^+$.

Example 32, cis-N-(8-(6-cyanopyridin-2-yl)-1,2,3,4,10,14b-hexahydro-10-methyldibenzo[b,f]pyrido[1,2-d][1,4]diazepin-2-yl)-2,2,2-trifluoroacetamide (9: $R_2$=$COCF_3$; $R_8$=$C_6H_3N_2$)

This compound was prepared, in an analogous manner as described in Example 12, (9, $R_2$=$COCF_3$ $R_8$=Br), to afford cis-N-(8-(6-cyanopyridin-2-yl)-1,2,3,4,10,14b-hexahydro-10-methyl-dibenzo[b,f]pyrido[1,2-d][1,4]diazepin-2-yl)-2,2,2-trifluoroacetamide (9: $R_2$=$COCF_3$; $R_8$=$C_6H_3N_2$) (58%). Data: (m/z)=478 (M+H)$^+$.

Example 33 cis-N-[8-(5-ethyl-1,2,4-oxadiazol-3-yl)-1,2,3,4,10,14b-hexahydro-10-methyldibenzo[b,f]pyrido[1,2-d][1,4]diazepin-2-yl]-2,2,2-trifluoroacetamide (9: $R_2$=$COCF_3$; $R_8$=$C_4H_5N_2O$)

To a stirred solution of (9: $R_2$=$COCF_3$; $R_8$=CN) (391 mg, 0.980 mmol) and triethylamine (212 μL, 1.51 mmol) in ethanol (5 ml) was charged hydroxylamine hydrochloride (102 mg, 1.47 mmol) and the reaction mixture was heated to 80° C. and held for 24 hours. The reaction mixture was reduced by rotary evaporation to yield an oil which was dissolved in DCM and washed with $H_2O$. The organics were then dried ($Na_2SO_4$) and concentrated under reduced pressure to yield an oil (420 mg, 100%). The crude product (31 mg, 0.072 mmol) was dissolved in toluene (1 ml) then pyridine (23 μL, 0.280 mmol) and propionyl chloride (12.5 μL, 0.140 mmol) were added and the reaction mixture was heated at 120° C. for 2 hours. The reaction mixture was washed with water, dried ($Na_2SO_4$) then concentrated under reduced pressure. The crude product was purified by reverse phase HPLC to afford cis-N-[8-(5-ethyl-1,2,4-oxadiazol-3-yl)-1,2,3,4,10,14b-hexahydro-10-methyldibenzo[b,f]pyrido[1,2-d][1,4]diazepin-2-yl]-2,2,2-trifluoroacetamide (9: $R_2$=$COCF_3$; $R_8$=$C_4H_5N_2O$) (6 mg, 18%). Data: (m/z)=472 (M+H)$^+$.

Example 34, cis-N-(1,2,3,4,10,14b-hexahydro-10-methyl-8-nitrodibenzo[b,f]pyrido-[1,2-d][1,4]diazepin-2-yl)-2-hydroxypropanamide (9: $R_2$=$COC_2H_5O$; $R_8$=$NO_2$)

This compound was prepared, in an analogous manner as described in Example 5, from (8: $R_8$=$NO_2$). The isolated compound was then taken up in EtOH and an 8% solution of NaOH was added. The reaction mixture was stirred at ambient temperature for 2 hours. Most of the EtOH was removed by under reduced pressure. $H_2O$ was then added and the product was extracted into DCM. The organics were then washed with saturated brine and dried ($Na_2SO_4$). The organics were concentrated under reduced pressure and the crude product was purified by column chromatography over silica to afford cis-N-(1,2,3,4,10,14b-hexahydro-10-methyl-8-nitrodibenzo[b,f]pyrido[1,2-d][1,4]diazepin-2-yl)-2-hydroxypropanamide (9: $R_2$=$COC_2H_5O$; $R_8$=$NO_2$) (49%). Data: (m/z)=397 (M+H)$^+$.

Example 35, cis-N-(9-chloro-8-cyano-1,2,3,4,10,14b-hexahydro-10-methyldibenzo-[b,f]pyrido[1,2-d][1,4]diazepin-2-yl)-2,2,2-trifluoroacetamide (9, $R_2$=$COCF_3$; $R_8$=CN; $R_9$=Cl)

This compound was prepared, in an analogous manner as described in Example 3, from (9: $R_2$=$COCF_3$; $R_8$=Br; $R_9$=Cl), to afford cis-N-(9-chloro-8-cyano-1,2,3,4,10,14b-hexahydro-10-methyldibenzo[b,f]pyrido[1,2-d][1,4]diazepin-2-yl)-2,2,2-trifluoroacetamide (9, $R_2$=$COCF_3R_8$=$CNR_9$=Cl) (60%). Data: (m/z)=435 (M+H)$^+$.

Example 36, cis-N-(5-methoxypyridin-3-yl)-1,2,3,4,10,14b-hexahydro-10-methyl-2-(2,2,2-trifluoroacetylamino)dibenzo[b,f]pyrido[1,2-d][1,4]diazepine-8-carboxamide (9: $R_2$=$COCF_3$; $R_8$=$C_7N_7N_2O_2$)

To a stirred solution of (9: $R_2$=$COCF_3$; $R_8$=$CHO_2$, Example 4) (20 mg, 0.048 mmol) in DCM (0.5 ml) and DMF (2 drops) was added a solution of oxalyl chloride (6.8 µL, 0.078 mmol) in DCM (0.5 ml). The reaction mixture was stirred for 1 hour at room temperature. The solvent was then removed under reduced pressure and the resulting oil was dissolved in THF (0.5 ml). Triethylamine (7.3 µL, 0.052 mmol) was then added and the reaction mixture was cooled to 0° C. A solution of 5-amino-2-methoxypyridine (6.5 mg, 0.052 mmol) in THF (0.5 ml) was then added and the reaction mixture was allowed to stir at ambient temperature for 20 hours. The reaction was quenched by addition of NaHCO$_3$ solution in H$_2$O and the product was extracted into EtOAc, dried (Na$_2$SO$_4$) and concentrated under reduced pressure. The crude product was purified by column chromatography on silica to afford cis-N-(5-methoxypyridin-3-yl)-1,2,3,4,10,14b-hexahydro-10-methyl-2-(2,2,2-trifluoroacetylamino)dibenzo[b,f]pyrido-[1,2-d][1,4]diazepine-8-carboxamide (9: $R_2$=$COCF_3$; $R_8$=$C_7N_7N_2O_2$) (39%). Data: (m/z)=526 (M+H)$^+$.

Example 37, cis-1,2,3,4,10,14b-hexahydro-10,14-dimethyl-2-(2,2,2-trifluoroacetylamino)dibenzo[b,f]pyrido[1,2-d][1,4]diazepine-8-carboxamide (9: $R_2$=$COCF_3$; $R_8$=$CH_2NO$; $R_{14}$=$CH_3$)

This compound was prepared, in an analogous manner as described in Example 1, from (8: $R_8$=$CH_2NO$; $R_{14}$=$CH_3$), to afford cis-1,2,3,4,10,14b-hexahydro-10,14-dimethyl-2-(2,2,2-trifluoroacetylamino)dibenzo[b,f]pyrido[1,2-d][1,4]diazepine-8-carboxamide (9: $R_2$=$COCF_3$; $R_8$=$CH_2NO$; $R_{14}$=$CH_3$) (19%). Data: (m/z)=433 (M+H)$^+$.

Example 38, cis-2,2,2-trifluoro-N-[1,2,3,4,10,14b-hexahydro-8-(2-hydroxyacetyl)-10,14-dimethyldibenzo[b,f]pyrido[1,2-d][1,4]diazepin-2-yl]acetamide (9: $R_2$=CO—CF$_3$; $R_8$=$C_2H_3O_2$)

To a stirred solution of (9: 2-CF$_3$; 8-C$_2$H$_3$O) (660 mg, 1.58 mmol) in dioxane (20 ml) was charged a solution of bromine (68.4 µL, 1.58 mmol) in Et$_2$O (5 ml) was added dropwise. The reaction mixture was heated to 40° C. for 30 hours. The reaction was quenched by addition of NaHCO$_3$ solution in H$_2$O and the product was extracted into EtOAc, dried (Na$_2$SO$_4$) and concentrated under reduced pressure. The crude product was purified by column chromatography on silica to afford (9: $R_2$=$COCF_3$; $R_8$=$C_2H_2BrO$) (350 mg, 45%). The product (9: $R_2$=$COCF_3$; $R_8$=$C_2H_2BrO$) (170 mg, 0.343 mmol) was then dissolved in EtOH/H$_2$O (85:15) (20 ml) and sodium formate (140 mg, 2.058 mmol) was added portionwise. The reaction mixture was stirred at ambient temperature for 20 hours. The reaction was quenched by addition of NaHCO$_3$ solution in H$_2$O and the product was extracted into EtOAc, dried (Na$_2$SO$_4$) and concentrated under reduced pressure. The crude product was purified by reverse phase HPLC to afford cis-2,2,2-trifluoro-N-[1,2,3,4,10,14b-hexahydro-8-(2-hydroxyacetyl)-10,14-dimethyldibenzo[b,f]pyrido[1,2-d][1,4]diazepin-2-yl]acetamide (9: $R_2$=CO—CF$_3$; $R_8$=$C_2H_3O_2$) (46 mg, 31%). Data: (m/z)=434 (M+H)$^+$.

Example 39, cis-1,2,3,4,10,14b-hexahydro-10-methyl-N-propyl-2-(2,2,2-trifluoroacetylamino)dibenzo[b,f]pyrido[1,2-d][1,4]diazepine-8-carboxamide (9: $R_2$=$COCF_3$; $R_8$=$C_4H_8NO$)

This compound was prepared, in an analogous manner as described in Example 36, from (9: $R_2$=$COCF_3$; $R_8$=$CHO_2$, Example 4), to afford cis-1,2,3,4,10,14b-hexahydro-10-methyl-N-propyl-2-(2,2,2-trifluoroacetylamino)dibenzo[b,f]pyrido[1,2-d][1,-4]diazepine-8-carboxamide (9: $R_2$=$COCF_3$; $R_8$=$C_4H_8NO$) (27%). Data: (m/z)=461 (M+H)$^+$.

Example 40, cis-2,2,2-trifluoro-N-[1,2,3,4,10,14b-hexahydro-10-methyl-8-(5-methoxymethyl-1,2,4-oxadiazol-3-yl)dibenzo[b,f]pyrido[1,2-d][1,4]diazepin-2-yl]acetamide (9: $R_2$=$COCF_3$; $R_8$=$C_4H_5N_2O_2$)

To a stirred solution of (9: $R_2$=$COCF_3$; $R_8$=CN) (391 mg, 0.980 mmol) and triethylamine (212 µL, 1.51 mmol) in ethanol (5 ml) was charged hydroxylamine hydrochloride (102 mg, 1.47 mmol) and the reaction mixture was heated to 80° C. and held for 24 hours. The reaction mixture was reduced by rotary evaporation to yield an oil which was dissolved in DCM and washed with H$_2$O. The organics were then dried (Na$_2$SO$_4$) and concentrated under reduced pressure to yield an oil (420 mg, 100%). The crude product (60 mg, 0.140 mmol) was dissolved in pyridine (1 ml) and methoxyacetyl chloride (25.5 µL, 0.280 mmol) was added then the reaction mixture was heated at reflux for 3 hours. The reaction mixture was washed with water, dried (Na$_2$SO$_4$) then concentrated under reduced pressure. The crude product was purified by reverse phase HPLC to afford cis-2,2,2-trifluoro-N-[1,2,3,4,10,14b-hexahydro-10-methyl-8-(5-methoxymethyl-1,2,4-oxadiazol-3-yl)dibenzo[b,f]pyrido[1,2-d][1,4]diazepin-2-yl]acetamide (9: $R_2$=$COCF_3$; $R_8$=$C_4H_5N_2O_2$) (12 mg, 18%). Data: (m/z)=488 (M+H)$^+$.

Example 41, cis-2,2,2-trifluoro-N-[1,2,3,4,10,14b-hexahydro-10-methyl-8-(3-methoxy-pyridin-5-yl)dibenzo[b,f]pyrido[1,2-d][1,4]diazepin-2-yl]acetamide (9: $R_2$=$COCF_3$; $R_8$=$C_6H_6NO$)

This compound was prepared, in an analogous manner as described for 12, from (9: $R_2$=$COCF_3$; $R_8$=Br), to afford cis-2,2,2-trifluoro-N-[1,2,3,4,10,14b-hexahydro-10-methyl-8-(3-methoxy-pyridine-5-yl)dibenzo[b,f]pyrido[1,2-d][1,4]diazepin-2-yl]acetamide (9: $R_2$=$COCF_3$; $R_8$=$C_6H_6NO$) (54%). Data: (m/z)=483 (M+H)$^+$.

Example 42, cis-N-(12-cyano-1,2,3,4,10,14b-hexahydro-10-methyl-8-nitro-dibenzo-[b,f]pyrido[1,2-d][1,4]diazepin-2-yl)-2,2,2-trifluoroacetamide (9: $R_2$=$COCF_3$; $R_8$=$NO_2$; $R_{12}$=CN)

This compound was prepared, in an analogous manner as described in Example 2, from (9: $R_2$=$COCF_3$; $R_{12}$=CN), to afford cis-N-(12-cyano-1,2,3,4,10,14b-hexahydro-10-methyl-8-nitro-dibenzo[b,f]pyrido[1,2-d][1,4]diazepin-2-yl)-2,2,2-trifluoroacetamide (9: $R_2$=$COCF_3$; $R_8$=$NO_2$; $R_{12}$=CN) (10%). Data: (m/z)=446 (M+H)$^+$.

Example 43, cis-N-(8,13-dibromo-1,2,3,4,10,14b-hexahydro-10,14-dimethyldibenzo-[b,f]pyrido[1,2-d][1,4]diazepin-2-yl)-2,2,2-trifluoroacetamide (9: $R_2$=$COCF_3$; $R_8$=Br; $R_{13}$=Br; $R_{14}$=CN)

This compound was prepared, in an analogous manner as described in Example 3, from (9: $R_2$=COCF$_3$; $R_{14}$=CN) to afford cis-N-(8,13-dibromo-1,2,3,4,10,14b-hexahydro-10,14-dimethyldibenzo[b,f]pyrido[1,2-d][1,4]diazepin-2-yl)-2,2,2-trifluoroacetamide (9: $R_2$=COCF$_3$; $R_8$=Br; $R_{13}$=Br; $R_{14}$=CN) (33%). Data: (m/z)=548 (M+H)$^+$.

Example 44, cis-N-[1,2,3,4,10,14b-hexahydro-10-methyl-8-(pyridin-4-yl)-dibenzo-[b,f]pyrido[1,2-d][1,4]diazepin-2-yl)-methanesulfonamide (9: $R_2$=S(O)$_2$CH$_3$; $R_8$=4-C$_5$H$_4$N)

To a stirred solution of (8; $R_8$=4-C$_5$H$_4$N) (200 mg, 0.54 mmol) in dichloromethane (10 ml) was added triethylamine (81 μL) and methanesulphonylchloride (45 μL), maintaining the temperature at 0° C. during the course of the addition. The reaction mixture was then stirred 2 hours at ambient temperature. The reaction was quenched with water and washed with saturated aqueous sodium hydrogen carbonate, brine and dried over magnesium sulphate. The reaction mixture was concentrated under reduced pressure and the crude product was purified by column chromatography on silica to afford cis-N-[1,2,3,4,10,14b-hexahydro-10-methyl-8-(pyridin-4-yl)-dibenzo[b,f]pyrido-[1,2-d][1,4]diazepin-2-yl)-methanesulfonamide (9: $R_2$=S(O)$_2$CH$_3$; $R_8$=4-C$_5$H$_4$N) (160 mg, 66%). Data: (m/z)=449 (M+H)$^+$.

Example 45, cis-N-(1,2,3,4,10,14b-hexahydro-10-methyl-8-cyanodibenzo[b,f]pyrido-[1,2-d][1,4]-diazepin-2-yl)-N'methyl-N'methoxyurea (9: $R_2$=CO N(Me)OMe, $R_8$=CN)

To a stirred solution of cis-N-(8-cyano-1,2,3,4,10,14b-hexahydro-10-methyldibenzo-[b,f]pyrido[1,2-d][1,4]diazepin-2-yl)-2,2,2-trifluoroacetamide (9: $R_2$=COCF$_3$; $R_8$=CN) (4.36 g, 10.9 mmol) in EtOH (72 ml) was added 2N NaOH (19.2 ml). The reaction mixture was stirred overnight at ambient temperature, then the reaction mixture was poured into water and extracted with EtOAc. The organic layer was washed with H$_2$O, then saturated brine, then dried (Na$_2$SO$_4$) and concentrated under reduced pressure to afford crude (8: $R_8$=CN) (3.04 g, 92%). Data: (m/z)=305 (M+H)$^+$.

To a stirred solution of (8: $R_8$=CN) (200 mg, 0.658 mmol) in EtOAc (8 ml) was added a catalytic amount of activated charcoal and trichloromethylchloroformate (94.8 μl, 0.197 mmol). The reaction mixture was stirred at reflux for 2 hours. The reaction mixture was filtered over dicalite and concentrated under reduced pressure to afford crude (8: isocyanate on position 2 (NCO), $R_8$=CN) (217 mg, 100%). Data: (m/z) =331 (M+H)$^+$.

To a stirred solution of (8: (NHR$_2$=NCO, $R_8$=CN) (54 mg, 0.164 mmol) in EtOAc (10 ml) was added a solution of N,O-dimethylhydroxylamine hydrochloride (80 mg, 0.197 mmol) with triethylamine (23.7 μl, 0.197 mmol) in EtOAc (5 ml). The reaction mixture was stirred at 50° C. for 2 days and then poured in water and extracted with EtOAc. The organic layer was washed with H$_2$O and saturated brine, then dried (Na$_2$SO$_4$) and concentrated under reduced pressure to afford after purification (9: $R_2$=CON(Me)OMe, $R_8$=CN) (5.9 mg, 9.2%). Data: (m/z)=392 (M+H)$^+$.

Example 46

Glucocorticoid Receptor Binding Activity

The affinity of compounds was tested using a Glucocorticoid Receptor Competitor Assay kit (PanVera®). Components of the kit were thawed from −80° C. on ice (Fluormone GS1, recombinant human-GR (GR)) or at room temperature (GR screening buffer, stabilising peptide and DTT). 10 mM test compounds were manually diluted to 20 μM then serially diluted to a final concentration range of 10 μM to 0.1 nM using the BioMek 2000 (Beckman-Coulter) into a black walled 384 welled plate (Matrix technologies). In the following order: fluormone GS1 (1 nM final concentration) is added to all wells excluding the buffer control wells, GR (4 nM final concentration) is added to all wells except minimum and buffer control wells, cortisol (10 μM final concentration) is added to fluormone GS1 control wells only, buffer is added to all wells to a final volume of 40 μl. The plate is covered and incubated at room temperature with agitation for 90 minutes. Readings were taken using the Analyst (LJL) in fluorescence polarisation reading mode. The MilliP ratio is calculated from cps readings obtained in parallel and perpendicular mode. The percent effect of the bound ligand is calculated at each concentration and the dose response curves plotted allowing the EC$_{50}$ to be calculated. This is compared to the known standard (11β,17β)-1-(1,3-benzodioxol-5-yl)-17-hydroxy-17-(1-propynyl)estra-4,9-dien-3-one (CAS No. 189035-07-2), EC$_{50}$=10$^{-8}$M). All compounds exemplified have binding activities <2×10$^{-8}$M.

Example 47

Functional Responses In Vitro

To quantify the ability of compounds to inhibit inflammatory gene expression in vitro, responses of compounds were evaluated in the human cell line U$_2$OS that was stably transfected with human recombinant GR DNA. U$_2$OS cells were stimulated with TNFα and IFNγ which leads to the secretion of MCP-1 in the supernatant. Secretion of MCP-1 was quantified indirectly by the use of two anti-human-MCP-1 antibodies, one labeled with the fluorescent donor Europium, the second one labeled with the fluorescent acceptor Allophycocyanin (APC). Secretion of MCP-1 in supernatant is quantified by measuring the emission wavelength of APC (665 nm) when Europium is excited at 340 nm. The ability of compounds (prednisolone or compounds according to formula I) to inhibit MCP-1 expression was quantified and EC$_{50}$ values were calculated. Examples 1, 2, 10, 11 and 14-24 showed an EC$_{50}$ of 0.2-2 nM whereas the value found for prednisolone was 2 nM.

Example 48

Anti-inflammatory Activity in vivo

The potency of compounds to inhibit inflammation was quantified in a model in which mice were treated with lipopolysaccharide (LPS). Anti-inflammatory effects were quantified as inhibition of LPS-induced TNFα (S. R. Hyde & R. E. McCallum, Infection & Immunity, 60; 976-982 (1992)). Mice were treated i.p. with 0.5 mg/kg LPS. Compounds (prednisolone or compounds according to formula I) were dosed systemically by either oral or subcutaneous administration at 1 hour before the induction with LPS. 1½ hours after LPS induction, serum was collected and mice were sacrificed. TNFα levels in serum were quantified using a commercially available Elisa-kit according to the descriptions of the supplier. Both prednisolone as well as compounds according to examples 2-7, 9 and 31, dose-dependently inhibited TNFα (ED$_{50}$: 0.5-20 mg/kg as compared to 0.5 for prednisolone).

Example 49

Anti-arthritic Activity in vivo

The ability of compounds to inhibit arthritis was tested in a Collagen type II-Induced Arthritis model in mice (D. E.

Trentham et al. J Exp Med 146; 857-868 (1977)). In this model male Dba/1 mice were immunized and boosted (after 3 weeks) with Collagen. Arthritis is scored as swelling of paws. Mice that develop arthritis are treated for 3 weeks either with prednisolone or compounds according to formula I, either orally or subcutaneously (the therapeutic model). Alternatively, treatment with prednisolone or compounds according to formula I, either orally or subcutaneously starts before the onset of arthritis (the semi-therapeutic model). In both the therapeutic as well as the semi-therapeutic model, further development of arthritis is scored as paw swelling 3 times a week. After 3 weeks, mice are sacrificed. Potency of compounds to inhibit arthritis is quantified as the ability to inhibit paw swelling. Both prednisolone as well as the examples (examples 2-5) tested (at a dose of 10 or 20 mg/kg) are able to significantly inhibit arthritis.

What is claimed is:

1. A compound according to formula I:

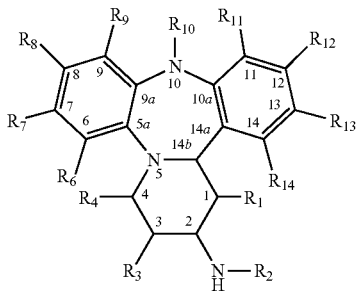

Formula I or a pharmaceutically acceptable salt thereof, wherein $R_1$ is H or (1-4C)alkyl;
$R_2$ is —C(O)$R_{15}$ or —S(O)$_2R_{15}$;
$R_3$ is H, (1-4C)alkyl or —O$R_{16}$;
$R_4$ is H, (1-4C)alkyl or —O$R_{16}$;
$R_6$ is H, —C(H)NO$R_{16}$;
$R_7$ is H, halogen or cyano;
or $R_7$ is (1-6C)alkyl, (2-6C)alkenyl or (2-6C)alkynyl, all three optionally substituted with OH, halogen or NH$_2$;
or $R_7$ is —C(H)NO$R_{16}$, —O$R_{16}$, —C(O)O$R_{16}$ or —C(O)$R_{16}$;
$R_8$ is cyano;
or $R_8$ is (1-6C) alkyl, (2-6C)alkenyl, (2-6C)alkynyl or —O(1-6C)alkyl, all substituted with amino, hydroxyl or halogen;
or $R_8$ is (hetero)aryl, optionally substituted with cyano, halogen, (1-4C)alkyl, (1-4C)alkoxy or (1-4C)alkoxy(1-4C)alkyl;
or $R_8$ is —C(H)NO$R_{16}$, —C(O)NH$R_{17}$, —C(O)$R_{18}$, —C(O)O$R_{19}$, or —C(1-4C)alkylNO$R_{21}$;
$R_9$ is H, halogen, cyano or (1-4C)alkyl optionally substituted with halogen
$R_{10}$ is H or (1-4C)alkyl;
$R_{11}$ is H;
$R_{12}$ is H, cyano or (1-4C)alkyl;
$R_{13}$ is H, (1-4C)alkyl, halogen or formyl;
$R_{14}$ is H, halogen, cyano, (1-4C)alkyl, (2-6C)alkenyl, C(O)$R_{21}$ or (hetero)aryl;
$R_{15}$ is H;
or $R_{15}$ is (1-6C)alkyl, (2-6C)alkenyl, (2-6C)alkynyl, —O(2-6C)alkyl, —O(2-6C)alkenyl or —O(2-6C)alkynyl, all optionally substituted with one or more OH, halogen, cyano or (hetero)aryl;
or $R_{15}$ is (hetero)aryl, optionally substituted with (1-4C)alkyl, halogen, cyano, nitro or amino;
or $R_{15}$ is NH$_2$, (di)(1-4C)alkylamino, (1-4C)alkyl(1-4C)alkoxyamine, (1-4C)alkylthio(1-4C)alkyl or (1-4C)alkoxy(1-4C)alkyl;
each $R_{16}$ independently is H, (1-6C)alkyl, (2-6C)alkenyl or (2-6C)alkynyl;
$R_{17}$ is H, (1-4C)alkoxy or (3-6C)cycloalkyl;
or $R_{17}$ is (1-6C)alkyl, optionally substituted with halogen;
or $R_{17}$ is (hetero)aryl, optionally substituted with halogen, (1-4C)alkyl or (1-4C)alkoxy;
$R_{18}$ is H, NH$_2$, —C(O)$R_{21}$ or —S(1-4C)alkyl;
or $R_{18}$ is (1-4C)alkyl, optionally substituted with OH, halogen or cyano;
$R_{19}$ is H or (1-6C)alkyl, optionally substituted with OH or halogen, and
each $R_{21}$ independently is H or (1-6C)alkyl.

2. The compound according to claim 1 wherein $R_7$ is H or halogen or O$R_{16}$.

3. The compound according to claim 1 wherein $R_7$ is H.

4. The compound according to claim 1 wherein $R_{10}$ is methyl.

5. The compound according to claim 1 wherein each $R_{16}$ is independently H or (1-6C)alkyl.

6. The compounds according to claim 1 wherein $R_2$ is C(O)$R_{15}$.

7. The compound according to claim 1 wherein $R_{15}$ is (1-4C)alkyl, optionally substituted with halogen.

8. The compound according to claim 7 wherein $R_{15}$ is trifluoromethyl.

9. The compound according to claim 1 wherein each $R_{21}$ is independently (1-4C)alkyl.

10. The compound according to claim 1 wherein $R_8$ is cyano or C(O)$R_{18}$;
or $R_8$ is (hetero)aryl, optionally substituted with cyano, (1-4C)alkyl, (1-4C)alkoxy, or (1-4C)alkoxy(1-4C)alkyl.

11. The compound according to claim 1 wherein $R_8$ is cyano or pyridyl.

* * * * *